United States Patent [19]

Suzuki

[11] 4,338,402

[45] Jul. 6, 1982

[54] ARTIFICIAL INSEMINATION INSTRUMENT FOR LIVESTOCK

[75] Inventor: Teruaki Suzuki, Hamamatsu, Japan

[73] Assignee: Kabushikikaisha Seisan Nipponsha Hamamatsu-Ko, Tokyo, Japan

[21] Appl. No.: 155,031

[22] Filed: Jun. 2, 1980

[51] Int. Cl.³ .............................................. C12M 1/00

[52] U.S. Cl. .................................... 435/287; 128/1 R

[58] Field of Search ............................ 128/1; 206/205; 435/287, 2 R; 220/426, 428; 119/1

[56] References Cited

U.S. PATENT DOCUMENTS 2,315,425 3/1943 Hill et al. ............................ 435/2 X 3,909,363 9/1975 Bucalo ............................ 435/296 X

*Primary Examiner*—Stephen C. Pellegrino

*Attorney, Agent, or Firm*—William A. Drucker

[57] ABSTRACT

A storage device for semen, for use in artificial insemination of livestock has a body with an internal space divided into a semen chamber and a serum chamber by a dialysis film. The semen chamber can be connected to (a) a pump, and (b) an injector device. The injector device has a tubular body carrying a removable injection tube which is adjustable longitudinally of the body and can be fully retracted within a radially-bulged end zone of the body. In a method of use, the bulged end of the body is inserted into the cervical canal, with the injection tube retracted. The injection tube is then adjusted to protrude into the uterine cavity, and the pump is operated to force semen from the semen chamber through the injection tube into the uterine cavity.

4 Claims, 4 Drawing Figures

ARTIFICIAL INSEMINATION INSTRUMENT FOR LIVESTOCK

BACKGROUND OF THE INVENTION

This invention relates to an artificial insemination instrument for livestock, particularly swine.

In the art of artificial insemination of livestock, it is known that the sperms of swine are shorter lived than those of other livestock, and hence long-time preservation of swine semen is attended by difficulties. In order to popularise artificial insemination of swine, it is necessary to allow easy access to semen of choice boars, and to ensure easy treatment thereof so that any average farmer can preserve and use such semen without requiring any specific skill nor any complicated equipment. However, as things stand now, there are few farmhouses which are furnished with a refrigerator suitable for preservation of semen, and in most cases, semen is procured from a dealer and inseminated each time a breed sow comes into heat.

Also, in the operation for injecting the thus procured semen into the uterine cavity, it is usual to suck up semen into an injector from a container, then insert the injector into the vaginal region and inject the semen. In such an operation, however, semen often flows back from the cervical canal, resulting in insufficient injection of semen into the uterine cavity. Also, in case of performing such insemination on two or more sows successively by using a single injector, it needs to disinfect the injector which touches the cervical canal with an antiseptic solution or boiling water at each time of use, because otherwise an undesirable effect might be given to the sperms and reduce the impregnation rate. Thus, the currently practised semen injecting operation is not easy and involves many difficult problems.

OBJECT OF THE INVENTION

In view of the above, the present invention has for its object to provide an improved instrument for artificial insemination of livestock, particularly swine, capable of facilitating semen preservation and elongation of its shelf life, and allowing immediate injection of semen from the injector with no need of transfusing semen from a preservation container into the injector. It is also an object to provide an injector which prevents backflow of semen and can be securely inserted deep into the cervical canal. It is a further object to provide an injector in which the portion which touches the cervical canal is easily replaceable, thereby avoiding the necessity of disinfection at each time of use of the instrument. In general, it is the object of the invention to provide a device which is very sanitary and which provides a marked improvement in impregnation rate.

BRIEF DESCRIPTION OF THE DRAWINGS

The invention is now described in detail with reference to an embodiment thereof shown in the accompanying drawings.

In the drawings.

DESCRIPTION OF THE PREFERRED EMBODIMENT

The instrument according to this invention may be roughly divided into the following three parts: a semen reservoir 1, a semen injector 11 and a pump 10.

First, the semen reservoir 1 is described with reference to FIG. 1. It is to be noted that a dialysis preservation technique is employed for preservation of semen in this invention.

Figure 1:
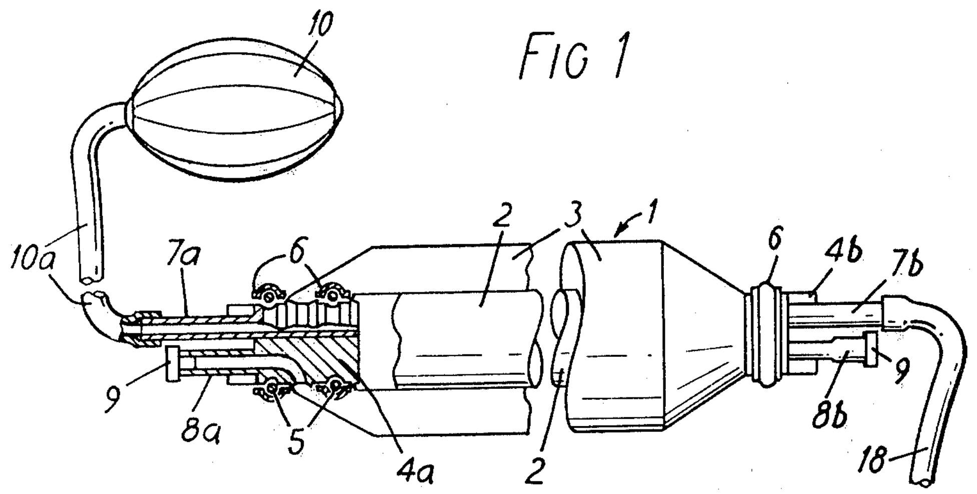
FIG. 1 is a side elevation, with parts broken away and parts shown in section, of a semen reservoir instrument.

In FIG. 1, reference numeral 2 indicates an inner cylinder made from a dialysis film (such as cellophane) and designed to contain semen therein. This inner cylinder 2 is disposed in an outer cylinder 3 made from a synthetic resin film such as polypropylene or vinyl, with a predetermined space provided therebetween to form a double-cylindered structure. The dialyzate (such as serum), which is a nutrient source for the semen, is filled in the space between said inner cylinder 2 and outer cylinder 3.

Both ends of said inner and outer cylinders 2, 3, are tightly sealed by packing members 4*a*, 4*b* each of which comprises O-rings 5 and associated rubber bands 6 for securing tightness. Each of said packing members 4*a*, 4*b* is provided with a first tube 7*a* (7*b*) which is communicated with the chamber defined by the inner cylinder 2 and a second tube 8*a* (8*b*) which is communicated with the chamber defined between said inner cylinder 2 and outer cylinder 3. The openings of these tubes 7*a*, 7*b*, 8*a*, 8*b*, can be sealed by a plug 9.

The two tubes 8*a*, 8*b* could both be arranged at a same end, and need not be at different ends as shown.

Figure 2:
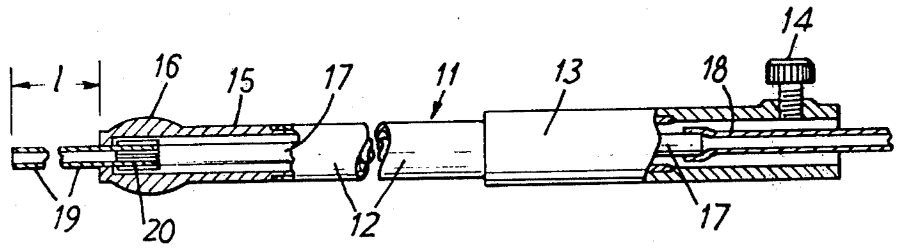
FIG. 2 is a side elevation, with parts shown in section, of the principal members of a semen injector.

The semen injector 11 is now described with reference to FIG. 2. In the drawing, reference numeral 12 denotes a holder pipe made of stainless steel or other suitable material and which has at its rear end a grip 13 and is also provided at its fore end with a removable cylindrical member 15 having a bulge 16 at an end. In this holder pipe 12 is slidably inserted a tube 17 of which the fore end is joined by a detachable joint 20 to an injection tube 19 which is arranged to be extendable telescopically through said end-bulged cylindrical member 15 telescopically. The rear end of said tube 17 is joined to a connection pipe 18 which is connected to one of said first tubes 7*a* or 7*b* provided in the packing members 4*a*, 4*b* of said semen reservoir 1. In the grip 13 is provided a stop screw 14 for fixing the injection tube 19 at a desired extended position. This stop screw 14 bears laterally against the pipe 18 to inhibit sliding movement of the tube 17.

Lastly, the pump 10 comprises a generally known type of rubber pouch and a pipe 10*a* connected thereto as shown in FIG. 1, said pipe 10*a* being connected to one of the first tubes 7*a* or 7*b* provided in the packing members 4*a*, 4*b* to transfer pressure into the inner cylinder 2.

For storing semen in the instrument of this invention, a semen collector is connected to one of the tubes 7*a* or 7*b* in the packing members 4*a*, 4*b* and the semen is charged into the inner cylinder chamber 2, and after completing this operation, the tube is again plugged. In the meantime, the dialyzate is poured into the outer cylinder chamber 3 from one of the second tubes 8*a* or 8*b*. Thus, the supplied semen is encompassed by the dialyzate with the dialysis film therebetween so that nutrition is given to the sperms. As the sperms are refrigerated at 15° C. under such a sealed condition, they can be kept live and active for as long as 7 to 8 days. Also, no specific refrigerator is required, and any ordinary domestic refrigerator can be used for preservation.

Figure 3:
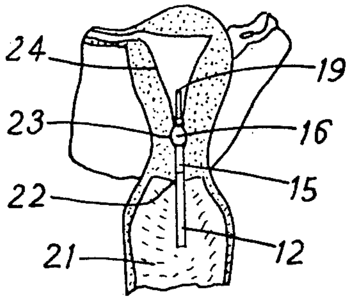
FIG. 3 is a schematic view to illustrate a method of insemination.

For performing insemination, firstly the connection pipe 18 of the semen injector 11 is connected to one of the first tubes *7a* or *7b* of the packing members *4a, 4b* of the semen reservoir 1 that has just been taken out of the refrigerator, and the other of said first tubes is connected to the pump 10 to thereby complete the set up. Then, with the semen reservoir 1 held by one hand of the operator or preferably suspended from the operator's neck, the holder pipe 122 of the semen injector 11 is inserted into the vagina 21 so that the end-bulged cylindrical member 15 is inserted through the outer os uteri 22 into the cervical canal 23 as shown in FIG. 3. With the cylindrical member 15 kept inserted in the cervical canal 23, the connection pipe 18 is moved forwards by a length of about 3 to 4 cm so that the injection tube 19 projects out by a length l from the cylindrical member 15 to advance deep into the uterine cavity 24. The injection tube 19 is fixed at this position by means of the stop screw 14 at the grip 13, and then the manual pump 10 is operated to inject semen in the inner cylinder chamber 2 into the uterine cavity 24 through the injection tube 19. During this semen injection operation, the bulge 16 at the end of the cylindrical member 15 presses tightly against the wall of the cervical canal 23 to inhibit backflow of semen, allowing the whole supply of semen to be injected into the uterine cavity 24.

After completion of injection, the holder pipe 12 is pulled out of the vagina 21 and the cylindrical member 15 at the end thereof is removed to replace the injection tube 19 and tube 17 with new ones, and after setting them properly, the device is used for the next run of insemination operation.

Figure 4:
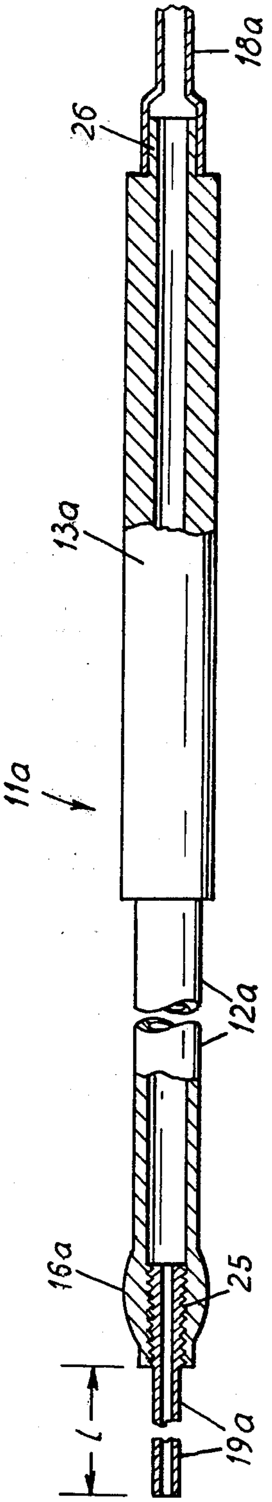
FIG. 4 is an elevation, with parts shown in section, of a modification.

Referring now to FIG. 4, there is shown a modified form of semen injector. As compared with the structure described above with reference to FIG. 2, in the modified instrument, the stop screw 14, tube 17 and joint 20 are eliminated. The injector tube **19*a* is modified so as to be attached by threading to a modified bulge 16*a* formed directly on the end of a modified holder pipe 12*a*. This permits the projecting length l of the tube 19*a* to be easily adjusted by rotation relative to the bulge 16*a*, and the tube 19*a* can be readily removed and replaced. The structure is also simplified in that the pipe 18*a* is now directly connected to a reduced nipple 26 formed on the end of the modified grip 13*a***.

Thus, with the device of this invention, adopting the dialytic preservation method, the reserve of semen can be stored for a long time in an ordinary type of refrigerator, and in the insemination operation, such reservoir can immediately serve as a semen supply tank, allowing injection of semen with no risk of exposure to the outer air, thus eliminating the problem of mixing of sundry germs or degeneration of semen and also allowing easy preparation for the injection operation.

Further, owing to prolongation of the semen shelf life, it is unnecessary to take the trouble of procuring semen each time a sown comes into heat, and semen can be readily used whenever it is needed.

Further, since an end-bulged cylindrical portion is provided at the end of the holder pipe of the semen injector, and the injection tube can be extended out by a desired length from said cylindrical portion, said injection tube can be inserted deep into the cervical canal with no risk of injuring the uterus by the instrument while preventing backflow of semen, so that the semen maintaining high spermal activity owing to dialytic preservation can be injected sufficiently into the uterine cavity to improve the fertilisation rate.

In addition, since both the injection tube and tube 17 can be easily removed from the holder pipe and are replaceable with new ones after each use for an injection operation, disinfection of the principal parts of the instrument is unnecessary to promote efficiency of the injection work while allowing always clean and hygienic insemination operation.

I claim:

1. A storage device for semen, for use in artificial insemination of livestock, comprising a body including an internal space, a dialysis film sealed to the body within said space and dividing said space into a first chamber and a second chamber, two first conduits in said body communicating with said first chamber, at least one second conduit in said body communicating with said second chamber, and means for stoppering said at least one second chamber.

2. A storage device for semen, as claimed in claim 1, comprising a respective external tube on said body communicating with each of said first conduits, for attachment respectively of a pump means and a delivery tube.

3. A storage device for semen, as claimed in claim 1, wherein said body comprises a pair of end members in each of which one of said first and second conduits is provided, an inner tube of said dialysis film sealed to said end members and bounding said first chamber, and an outer tube sealed to said end members and bounding said second chamber externally of said first chamber.

4. A storage device for semen, as claimed in claim 3, wherein said inner tube and said outer tube are sealed to said end members by O-rings.

* * * * *